United States Patent
Bui et al.

(10) Patent No.: US 9,066,863 B2
(45) Date of Patent: Jun. 30, 2015

(54) SILKY-FEELING NON-AQUEOUS STRUCTURED COMPOSITION

(75) Inventors: Hy Si Bui, Piscataway, NJ (US);
Mohamed Kanji, Edison, NJ (US);
Anita Chon Tong, Westfield, NJ (US)

(73) Assignee: L'ORÉAL (FR)

( * ) Notice: Subject to any disclaimer, the term of this patent is extended or adjusted under 35 U.S.C. 154(b) by 0 days.

(21) Appl. No.: 13/583,674

(22) PCT Filed: Mar. 10, 2011

(86) PCT No.: PCT/US2011/027873
§ 371 (c)(1),
(2), (4) Date: Sep. 10, 2012

(87) PCT Pub. No.: WO2011/112797
PCT Pub. Date: Sep. 15, 2011

(65) Prior Publication Data
US 2013/0005832 A1    Jan. 3, 2013

Related U.S. Application Data

(60) Provisional application No. 61/312,452, filed on Mar. 10, 2010.

(51) Int. Cl.

| | | |
|---|---|---|
| *A61Q 19/00* | (2006.01) | |
| *A61K 9/06* | (2006.01) | |
| *A61K 8/04* | (2006.01) | |
| *A61K 8/31* | (2006.01) | |
| *A61K 8/34* | (2006.01) | |
| *A61K 8/44* | (2006.01) | |
| *A61K 8/891* | (2006.01) | |
| *A61K 8/895* | (2006.01) | |
| *A61K 47/18* | (2006.01) | |

(52) U.S. Cl.
CPC . *A61K 9/06* (2013.01); *A61K 8/042* (2013.01); *A61K 8/31* (2013.01); *A61K 8/342* (2013.01); *A61K 8/442* (2013.01); *A61K 8/891* (2013.01); *A61K 8/895* (2013.01); *A61K 47/18* (2013.01); *A61K 2800/31* (2013.01); *A61K 2800/5922* (2013.01); *A61Q 19/00* (2013.01)

(58) Field of Classification Search
CPC .............. A61Q 19/00; A61K 2800/31; A61K 2800/5922
See application file for complete search history.

(56) References Cited

U.S. PATENT DOCUMENTS

| | | |
|---|---|---|
| 4,291,018 A | 9/1981 | Oeda et al. |
| 5,424,070 A * | 6/1995 | Kasat et al. ................... 424/401 |
| 5,716,604 A * | 2/1998 | Coe et al. ......................... 424/65 |
| 7,758,848 B2 | 7/2010 | Lu et al. |
| 2002/0127192 A1 | 9/2002 | Murphy et al. |
| 2002/0159961 A1 | 10/2002 | Yamato et al. |
| 2004/0170586 A1 | 9/2004 | Ferrari et al. |
| 2004/0229984 A1 | 11/2004 | Yamato et al. |
| 2005/0220728 A1* | 10/2005 | Kanji et al. ...................... 424/59 |
| 2006/0110345 A1 | 5/2006 | Lu et al. |
| 2006/0134037 A1 | 6/2006 | Cropper et al. |
| 2007/0128233 A1 | 6/2007 | Lu et al. |
| 2007/0243151 A1 | 10/2007 | Healy |
| 2007/0258923 A1 | 11/2007 | Bui et al. |
| 2008/0057011 A1 | 3/2008 | Ferrari |
| 2008/0102048 A1 | 5/2008 | McDermott |
| 2009/0280076 A1 | 11/2009 | Yoshida et al. |
| 2009/0280077 A1 | 11/2009 | Yoshida et al. |
| 2009/0317345 A1 | 12/2009 | Joshi et al. |
| 2010/0203097 A1 | 8/2010 | Tanaka |
| 2012/0045493 A1 | 2/2012 | Popoff et al. |

OTHER PUBLICATIONS

International Search Report Application No. PCT/US2011/027873, dated Nov. 24, 2011.
International Search Report Application No. PCT/US2011/027866, dated Nov. 24, 2011.
International Search Report Application No. PCT/US2011/027877, dated Nov. 25, 2011.
International Search Report Application No. PCT/US2011/027880, dated Nov. 25, 2011.
International Search Report Application No. PCT/US2011/027887, dated Nov. 25, 2011.

* cited by examiner

*Primary Examiner* — Trevor Love
(74) *Attorney, Agent, or Firm* — Lerner, David, Littenberg, Krumholz & Mentlik, LLP

(57) ABSTRACT

Disclosed is a non-aqueous, structured, gel-form composition containing: (a) a low molecular mass N-acyl glutamic acid diamide having a straight-chain alkyl group; (b) a low molecular mass N-acyl glutamic acid diamide having a branched-chain alkyl group; (c) at least one gel-promoting solvent; (d) at least one silicone elastomer; (e) at least one solvent capable of solubilizing the silicone elastomer; and (f) at least one active ingredient, wherein the composition has a hardness value ranging from about 30 to about 300 gf, a melting point of about 50° C. or higher, does not require use of wax as a structuring agent, and has a silky feeling when applied onto a keratinous substrate. Methods of making and using the compositions are also provided.

15 Claims, No Drawings

SILKY-FEELING NON-AQUEOUS STRUCTURED COMPOSITION

CROSS-REFERENCE TO RELATED APPLICATIONS

The present application is a national phase entry under 35 U.S.C. §371 of International Application No. PCT/U.S.2011/027873 filed Mar. 10, 2011, published in English, which claims priority from U.S. Provisional Patent Application No. 61/312,452, filed Mar. 10, 2010, all of which are incorporated herein by reference.

FIELD OF THE INVENTION

The present invention relates, in general, to a composition for application onto a targeted substrate. More particularly, the present invention relates to a non-aqueous, composition capable of forming a gel structure, and which have a silky feel, good pay-off, good storage stability, particularly with respect to variations in temperature, and does not require the use of wax as a structuring agent.

BACKGROUND OF THE INVENTION

Conventional structured compositions typically employ various types of waxes as structuring agents in order to form user-friendly products having good pay-off (a term used to describe both the amount of product applied onto a target substrate, as well as, the way the product distributes onto the substrate), and stability properties, particularly with respect to temperature stability. The problem with wax-based stick compositions is that they possess an undesirable waxy feel and inherently reduce the shine of any shine-imparting ingredients present in the stick composition.

Attempts have been made to formulate structured gel compositions in the absence of wax. For example, various types of polyamides have been commercialized as gellators/structuring agents in order to form solid compositions. Similarly, various glutamides, as well as various types of polyurethanes have also been commercialized in order to form solid, preferably clear, compositions. Such attempts, however, while successful at making solid compositions, possess numerous technical problems.

One of the technical problems associated with the above-referenced, commercial wax-free compositions involves their stability when exposed to elevated temperatures. It is imperative, from a practical point of view, that such compositions be able to withstand fluctuations in temperature during conventional storage conditions without becoming too soft, thereby negatively impacting their use profile. In order to avoid such stability issues, the composition must possess a certain melting point profile.

Another technical problem relates to the way in which the composition is deposited onto a target substrate, also referred to as "pay-off". Poor pay-off, defined as too much deposit, too little deposit, or lack of uniformity of deposit, is primarily associated with the hardness/elasticity of the structured composition. Thus, in order to avoid such deposit issues, particularly with respect to color deposit, it is necessary that the composition possess certain hardness/elasticity properties.

It is therefore an object of the present invention to provide a non-aqueous, structured, gel-form composition having a silky feel, is capable of carrying various types of active ingredients and that does not suffer from the aforementioned technical problems.

SUMMARY OF THE INVENTION

An aspect of the present invention is directed to a non-aqueous composition that is capable of forming a gel structure, e.g., a soft gel or a hard or molded gel (such as a gel stick), containing: (a) a low molecular mass N-acyl glutamic acid diamide having a straight-chain alkyl group; (b) a low molecular mass N-acyl glutamic acid diamide having a branched-chain alkyl group; (c) at least one gel-promoting solvent; (d) at least one silicone elastomer; (e) at least one solvent capable of solubilizing the silicone elastomer; and (f) at least one active ingredient, wherein the composition has a hardness value ranging from about 30 to about 300 gramforce (gf), a melting point of about 50° C. or higher, and does not require use of wax as a structuring agent (e.g., is free of wax). The inventive compositions, which may transparent or colored in appearance, have a silky feeling when applied onto a keratinous substrate.

Another aspect of the present invention is directed to a process for making the non-aqueous composition comprising: (a) providing a low molecular mass N-acyl glutamic acid diamide having a straight-chain alkyl group; (b) providing a low molecular mass N-acyl glutamic acid diamide having a branched-chain alkyl group; (c) providing at least one gel-promoting solvent; (d) providing at least one silicone elastomer; (e) providing at least one solvent capable of solubilizing the silicone elastomer; (f) providing at least one active ingredient; (g) mixing (a)-(f), at an elevated temperature generally ranging from about 90° C. to about 125° C., to form a heated composition; and (h) cooling the heated composition to form the non-aqueous composition, wherein the composition has a hardness value ranging from about 30 to about 300 gf, and a melting point of about 50° C. or higher. Preparing the compositions at these temperatures minimizes both the cost, and degree of manufacturing difficulty.

DETAILED DESCRIPTION OF THE INVENTION

Other than in the operating examples, or where otherwise indicated, all numbers expressing quantities of ingredients and/or reaction conditions are to be understood as being modified in all instances by the term "about", which as used herein refers to ±10-±15% of the referenced value.

"Volatile", as used herein, means having a flash point of less than about 100° C.

"Non-volatile", as used herein, means having a flash point of greater than about 100° C.

"Transparent" is defined as having the property of transmitting rays of light through its substance so that bodies situated beyond or behind can be distinctly seen. As used herein, "structured" means gelled and/or rigidified.

Low Molecular Mass Organogellators

The at least one straight-chain low molecular mass (wherein the term "low molecular mass" as used herein refers to a molecular mass from greater than zero up to about 2,000 daltons) organogellator may be chosen, for example, from an N-acyl glutamic acid diamide having a straight-chain alkyl group, such as dibutyl lauroyl glutamide.

The at least one branched-chain low molecular mass organogellator may be chosen, for example, from an N-acyl glutamic acid diamide having a branched-chain alkyl group, such as dibutyl ethylhexanoyl glutamide.

The straight-chain low molecular mass organogellator is employed in an amount of from about 0.1 to about 10% by weight, such as from about 0.5 to about 5% by weight, and from about 1 to about 3% by weight, all weights being based on the total weight of the composition.

Similarly, the branched-chain low molecular mass organogellator is employed in an amount of from about 0.1 to about 10% by weight, such as from about 0.5 to about 5% by weight, and from about 1 to about 3% by weight, all weights being based on the total weight of the composition.

In order to make a composition which is clear or transparent appearance (in which case they contain no pigment or less than about 0.5% pigment), the composition should employ the low molecular mass organogellators in a total amount of less than about 7% by weight, based on the weight of the composition.

The dibutyl lauroyl glutamide is commercially available as GP-1 and the dibutyl ethylhexanoyl glutamide is commercially available as EB-21, both available from Ajinomoto of Fort Lee, N.J.

In a preferred embodiment, the straight-chain low molecular mass N-acyl glutamic acid diamide and branched-chain low molecular mass N-acyl glutamic acid diamide are employed in a ratio by weight of from about 1:1 to about 3:1, and preferably from about 1.5:1.

Gel-Promoting Solvent

The low molecular mass organogellators of the present invention are solubilized in a solvent that promotes gel formation. Suitable solvents include, for example, alcohols, monoalcohols, dialcohols, acids, esters, and the like. Polar and non-polar solvents may be utilized.

It is preferred to utilize a polar solvent. Preferred polar solvents include, but are not limited to, C2-C5 glycols, such as propylene glycol, butylene glycol and pentylene glycol. These solvents are believed to promote gel formation by inhibiting intercalation (intramolecular bonding) in the glutamide molecules. Other preferred solvents include, for example, octododecanol, isostearyl alcohol, and the like. Yet other preferred solvents include substituted hydrocarbyl siloxanes, as disclosed, for example, in U.S. Patent Application Publication 2004/0223936 A1. They are believed to promote hydrogen bond formation between molecules of the glutamides. One exemplary substituted hydrocarbyl siloxane is CARBINOL FLUID, bis-hydroxyethoxypropyl dimethicone, which is a hydrocarbyl functional organopolysiloxane having the formula, $R^1Me_2SiO(Me_2SiO)_xSiMe_2R^1$ where $R^1$ is $-(CH_2)_3OCH_2CH_2OH$, and x is such to provide the product with a viscosity of about 50 cS (mm$_2$/s) at 23° C. The solvents listed herein may be used individually or in combination of two or more.

It is preferred that the solvents be capable of dissolving said organogellators at a temperature of from about 90° C. to about 125° C.

The at least one gel-promoting solvent will typically be employed in an amount of from about 1 to about 20% by weight, such as from about 2 to about 10% by weight, and from about 3 to about 5% by weight, all weights being based on the total weight of the composition.

Silicone Elastomers

According to the present invention, compositions comprising at least one silicone elastomer are provided. Any cosmetically suitable silicone elastomer can be used in accordance with the present invention. Suitable silicone elastomers include, for example, emulsifying silicone elastomers such as polyglycerolated and/or hydrophilic emulsifying silicone elastomers such as alkoxylated silicone elastomers, and non-emulsifying silicone elastomers. Such silicone elastomers can be spherical or non-spherical.

Polyglycerolated Silicone Elastomers

Suitable polyglycerolated silicone elastomers include, for example, crosslinked elastomeric organopolysiloxanes that may be obtained by a crosslinking addition reaction of diorganopolysiloxane containing at least one hydrogen atom linked to silicon and of polyglycerolated compounds containing ethylenically unsaturated groups, especially in the presence of a platinum catalyst.

Preferably, the crosslinked elastomeric organopolysiloxane is obtained by a crosslinking addition reaction (A) of diorganopolysiloxane containing at least two hydrogens each linked to a silicone, and (B) of glycerolated compounds containing at least two ethylenically unsaturated groups, especially in the presence (C) of a platinum catalyst.

In particular, the organopolysiloxane may be obtained by reaction of a polyglycerolated compound containing dimethylvinylsiloxy end groups and of methylhydrogenopolysiloxane containing trimethylsiloxy end groups, in the presence of a platinum catalyst.

Compound (A) is the base reagent for the formation of elastomeric organopolysiloxane and the crosslinking is performed by an addition reaction of compound (A) with compound (B) in the presence of the catalyst (C).

Compound (A) is in particular an organopolysiloxane containing at least 2 hydrogen atoms linked to different silicon atoms in each molecule.

Compound (A) may have any molecular structure, in particular a linear chain or branched chain structure or a cyclic structure.

Compound (A) may have a viscosity at 25° C. ranging from 1 to 50,000 centistokes, especially in order to have good miscibility with compound (B).

The organic groups linked to silicon atoms of the compound (A) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. The said organic group is preferably chosen from methyl, phenyl and lauryl groups.

Compound (A) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, or dimethylsiloxane-methylhydrogenosiloxane-laurylmethylsiloxane copolymers containing trimethylsiloxy end groups.

Compound (B) may be a polyglycerolated compound corresponding to formula (B') below:

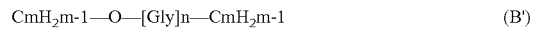

$$CmH_2m-1-O-[Gly]n-CmH_2m-1 \qquad (B')$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferably ranging from 2 to 5, and in particular equal to 3; Gly denotes:

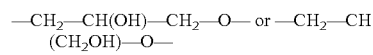

$-CH_2-CH(OH)-CH_2-O-$ or $-CH_2-CH(CH_2OH)-O-$

Advantageously, the sum of the number of ethylenic groups per molecule of compound (B) and of the number of hydrogen atoms linked to silicon atoms per molecule of compound (A) is at least 4.

It is advantageous for compound (A) to be added in an amount such that the molar ratio between the total amount of hydrogen atoms linked to silicon atoms in compound (A) and the total amount of all the ethylenically unsaturated groups in compound (B) is within the range from 1/1 to 20/1.

Compound (C) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in from 0.1 to 1,000 parts by weight, better still from 1 to 100 parts by weight, as clean platinum metal per 1,000 parts by weight of the total amount of compounds (A) and (B).

The polyglycerolated silicone elastomer may be conveyed in gel form in at least one hydrocarbon-based oil and/or one silicone oil.

Polyglycerolated silicone elastomers that may be used include, but are not limited to, those sold under the names "KSG-710", "KSG-810", "KSG-820", "KSG-830" and "KSG-840" by the company Shin-Etsu. Suitable polygycerolated silicone elastomers are also disclosed in U.S. Patent Application Publication No. 2005/0220728, the entire disclosure of which is hereby incorporated by reference.

Hydrophilic Emulsifying Silicone Elastomers

The term "hydrophilic emulsifying silicone elastomer" means a silicone elastomer comprising at least one hydrophilic chain other than a polyglycerolated chain as described above.

In particular, the hydrophilic emulsifying silicone elastomer may be chosen from polyoxyalkylenated silicone elastomers.

Suitable polyoxyalkylenated silicone elastomers include crosslinked organopolysiloxanes that may be obtained by a crosslinking addition reaction of diorganopolysiloxane containing at least one hydrogen linked to silicon and of a polyoxyalkylene containing at least two ethylenically unsaturated groups.

Preferably, the polyoxyalkylenated crosslinked organopolysiloxane is obtained by a crosslinking addition reaction (A1) of diorganopolysiloxane containing at least two hydrogens each linked to a silicon, and (B1) of polyoxyalkylene containing at least two ethylenically unsaturated groups, especially in the presence (C1) of a platinum catalyst, as described, for example, in U.S. Pat. Nos. 5,236,986 and 5,412,004, the entire disclosures of which are hereby incorporated by reference.

The organopolysiloxane may be obtained by reaction of polyoxyalkylene (especially polyoxyethylene and/or polyoxypropylene) containing dimethylvinylsiloxy end groups and of methylhydrogenopolysiloxane containing trimethylsiloxy end groups, in the presence of a platinum catalyst.

The organic groups linked to silicon atoms of the compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethylsiloxane-methylhydrogenosiloxane-laurylmethylsiloxane copolymers containing trimethylsiloxy end groups.

Compound (C1) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

Preferably, the polyoxyalkylenated silicone elastomers may be formed from divinyl compounds, in particular polyoxyalkylenes containing at least two vinyl groups, reacting with Si—H bonds of a polysiloxane.

The polyoxyalkylenated silicone elastomers may be conveyed in the form of a gel consisting of an elastomeric organopolysiloxane included in at least one hydrocarbon-based oil and/or one silicone oil.

Suitable polyoxyalkylenated elastomers are described in U.S. Pat. Nos. 5,236,986; 5,412,004; 5,837,793 and 5,811,487, the entire contents of which are incorporated herein by reference.

Suitable polyoxyalkylenated silicone elastomers that may be used include those sold under the names "KSG-21", "KSG-20", "KSG-30", "KSG-31", "KSG-32", "KSG-33", "KSG-210", "KSG-310", "KSG-320", "KSG-330", "KSG-340" and "X-226146" by the company Shin-Etsu, or "DC9010" and "DC9011" by the company Dow Corning.

Suitable hydrophilic emulsifying silicone elastomers are also disclosed in U.S. Patent Application Publication No. 2005/0220728, the entire disclosure of which is hereby incorporated by reference.

Non-Emulsifying Silicone Elastomers

The term "non-emulsifying" defines elastomers not containing a hydrophilic chain, such as polyoxyalkylene or polyglycerolated units.

The non-emulsifying silicone elastomer is preferably an elastomeric crosslinked organopolysiloxane that may be obtained by a crosslinking addition reaction of diorganopolysiloxane containing at least one hydrogen linked to silicon and of diorganopolysiloxane containing ethylenically unsaturated groups linked to silicon, especially in the presence of a platinum catalyst; or by dehydrogenation crosslinking coupling reaction between a diorganopolysiloxane containing hydroxyl end groups and a diorganopolysiloxane containing at least one hydrogen linked to silicon, especially in the presence of an organotin compound; or by a crosslinking coupling reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the elastomeric crosslinked organopolysiloxane is obtained by a crosslinking addition reaction (A2) of diorganopolysiloxane containing at least two hydrogens each linked to a silicon, and (B2) of diorganopolysiloxane containing at least two ethylenically unsaturated groups linked to silicon, especially in the presence (C2) of a platinum catalyst, as described, for example, in EP0295886A, the entire disclosure of which is hereby incorporated by reference.

The organopolysiloxane may be obtained by reaction of dimethylpolysiloxane containing dimethylvinylsiloxy end groups and of methylhydrogenopolysiloxane containing trimethylsiloxy end groups, in the presence of a platinum catalyst.

Compound (A2) is the base reagent for the formation of elastomeric organopolysiloxane, and the crosslinking is performed by an addition reaction of compound (A2) with compound (B2) in the presence of a catalyst (C2).

Compound (A2) is advantageously a diorganopolysiloxane containing at least two lower (for example C2-C4) alkenyl groups; the lower alkenyl group may be chosen from vinyl, allyl and propenyl groups. These lower alkenyl groups may be located in any position on the organopolysiloxane molecule, but are preferably located at the ends of the organopolysiloxane molecule. The organopolysiloxane (A2) may have a branched-chain, linear-chain, cyclic or network structure, but the linear-chain structure is preferred. Compound (A2) may have a viscosity ranging from the liquid state to the gum state. Preferably, compound (A2) has a viscosity of at least 100 centistokes at 25° C.

The organopolysiloxanes (A2) may be chosen from methylvinylsiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenylsiloxane-methylvinylsiloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

Compound (B2) is in particular an organopolysiloxane containing at least 2 hydrogens linked to silicon in each molecule and is thus the crosslinking agent for the compound (A2).

Preferably, the sum of the number of ethylenic groups per molecule of compound (A2) and the number of hydrogen atoms linked to silicon per molecule of compound (B2) is at least 4.

Compound (B2) may be in any molecular structure, especially of linear-chain or branched-chain structure, or cyclic structure.

Compound (B2) may have a viscosity at 25° C. ranging from 1 to 50,000 centistokes, especially in order to have good miscibility with compound (A).

It is advantageous for compound (B2) to be added in an amount such that the molar ratio between the total amount of hydrogen atoms linked to silicon in compound (B2) and the total amount of all of the ethylenically unsaturated groups in compound (A2) is within the range from 1/1 to 20/1.

Compound (B2) may be chosen from methylhydrogenopolysiloxanes containing trimethylsiloxy end groups, dimethylsiloxane-methylhydrogenosiloxane copolymers containing trimethylsiloxy end groups, and dimethylsiloxane-methylhydrogenosiloxane cyclic copolymers.

Compound (C2) is the crosslinking reaction catalyst, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in from 0.1 to 1,000 parts by weight, better still from 1 to 100 parts by weight, as clean platinum metal per 1,000 parts by weight of the total amount of compounds (A2) and (B2).

Other organic groups may be linked to silicon in the organopolysiloxanes (A2) and (B2) described above, for instance alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The elastomeric crosslinked organopolysiloxanes may be conveyed in the form of a gel consisting of an elastomeric organopolysiloxane included in at least one hydrocarbon-based oil and/or one silicone oil. The elastomeric crosslinked organopolysiloxanes may also be in powder form.

Suitable non-emulsifying silicone elastomers are described in JP61-194009 A, EP0242219 A, EP0295886 A and EP0765656 A, the entire contents of which are herein incorporated by reference.

Suitable non-emulsifying silicone elastomers that may be used include, but are not limited to, those sold under the names "DC 9040", "DC 9041", "DC 9509", "DC 9505" and "DC 9506" by the company Dow Corning.

Suitable non-emulsifying silicone elastomers are also disclosed in U.S. Patent Application Publication No. 2005/0220728, the entire disclosure of which is hereby incorporated by reference.

The non-emulsifying silicone elastomer may also be in the form of elastomeric crosslinked organopolysiloxane powder coated with silicone resin, especially with silsesquioxane resin, as described, for example, in U.S. Pat. No. 5,538,793, the entire content of which is herein incorporated by reference. Such elastomers are sold under the names "KSP-100", "KSP-101", "KSP-102", "KSP-103", "KSP-104" and "KSP-105" by the company Shin-Etsu.

Other elastomeric crosslinked organopolysiloxanes in the form of powders include hybrid silicone powders functionalized with fluoroalkyl groups, sold especially under the name "KSP-200" by the company Shin-Etsu; hybrid silicone powders functionalized with phenyl groups, sold especially under the name "KSP-300" by the company Shin-Etsu.

The silicone elastomer may be present in the compositions of the present invention in an amount of from about 1% to about 40% of the total weight of the composition, more preferably from about 5% to about 30% of the total weight of the composition, and most preferably from about 10% to about 20%, including all ranges and subranges therebetween.

Silicone Elastomer Solvents

Solvents capable of solubilizing the silicone elastomer include, for example, volatile and/or non-volatile oils. Such oils can be any acceptable oil including but not limited to silicone oils and/or hydrocarbon oils.

According to preferred embodiments, the solvent includes one or more volatile silicone oils. Examples of such volatile silicone oils include linear or cyclic silicone oils having a viscosity at room temperature less than or equal to 6cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |

TABLE 1-continued

| Compound | Flash Point (° C.) | Viscosity (cSt) |
|---|---|---|
| Dodecamethylcyclohexasiloxane (D6) | 93 | 7 |
| Decamethyltetrasiloxane (L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, volatile silicone oils that are linear may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to other preferred embodiments, the solvent includes one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched C8 to C16 alkanes such as C8 to C16 isoalkanes (also known as isoparaffins), isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
|---|---|
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

Examples of non-volatile oils that may be used in the present invention include, but are not limited to, polar oils such as:

a.—hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, quinoa oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

b.—synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

c.—synthetic ethers containing from 10 to 40 carbon atoms;

d.—$C_8$ to $C_{26}$ fatty alcohols, for instance oleyl alcohol; and e.—mixtures thereof.

Examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

In some embodiments of the present invention, it may be desirable to make the composition transparent in appearance.

One way of making the composition of the present invention transparent in appearance is by employing an appropriate solvent for the silicone elastomer. One such appropriate solvent is, for example, isododecane.

The silicone elastomer solvent will typically be employed in an amount of from about 5 to about 90% by weight, such as from about 10 to about 80% by weight, and all subranges therebetween, all weights based on the total weight of the composition.

Active Ingredients

The purpose of the non-aqueous, structured gel-form composition of the present invention is to carry active ingredients for application onto a variety of target substrates in a silky-feeling way. Various types of active ingredients may be carried by the composition. Examples of suitable active ingredients include, for example, colorants such as pigments, inks and lakes; dermatological ingredients such as sunscreen agents, anti-acne agents, anti-aging compounds; insect repelling agents; transdermal pharmaceutical compounds; deodorant and antiperspirant agents; perfumes; dye compounds; etc.

The type and amount of active ingredient to be employed will depend on the ultimate use of the composition, and are within the ordinary skill in the art. The active ingredient is present in amounts generally ranging from about 0.01 to 20wt % and in some embodiments from about 0.1 to about 10% by weight, based on the total weight of the composition. As stated above, the compositions of the invention that are transparent may contain no colorant or colorant in an amount less than about 0.5% by weight. Compositions that contain colorant and which are colored in appearance will generally contain more than about 0.5% colorant.

Moreover, due to its unique texture and feel, application of the composition onto a keratinous substrate such as hair, skin or nails, provides a more pleasing tactile experience, i.e., silky feeling, for the end-user.

The resultant composition should be stable under conventional storage conditions. In order to achieve storage stability, the composition must have a melting point of at least about 50° C. or higher, e.g., 70° C. or higher, or even 80° C. or higher.

The composition should also have good "pay-off", i.e., the ability to be elegantly and uniformly deposited onto a targeted substrate. This property is dependent on the hardness of the composition.

The hardness of the composition may, for example, be expressed in gramforce (gf). The composition of the present invention may, for example, have a hardness ranging from about 30 gf to about 300 gf, such as from about 50 gf to about 120 gf, and further such as from about 60 gf to about 100 gf.

Hardness is measured in one of two ways. A first test for hardness entails penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is known as the "cheese wire" method, which involves cutting an 8.1 mm or preferably 12.7 mm-diameter stick composition and measuring its hardness at 20° C. using a DFGHS 2 tensile testing machine from Indelco-Chatillon Co. at a speed of 100 mm/minute. The hardness value obtained from this method is expressed in grams as the shear force required to cut a stick under the above conditions. According to this method, the hardness of compositions according to the present invention which may be in stick form may, for example, range from 30 gf to 300 gf, such as from 30 gf to 250 gf, for a sample of 8.1 mm in diameter stick, and further such as from 30 gf to 200 gf, and also further such as from 30 gf to 120 gf for a sample of 12.7 mm in diameter stick.

The hardness of the composition of the present invention may be such that the compositions are self-supporting and can easily disintegrate to form a satisfactory deposit on a targeted substrate. In addition, this hardness may impart good impact strength to the inventive compositions, which may be molded, cast, or extruded, for example, in stick or dish form.

The present invention will be better understood from the examples which follow, all of which are intended for illustrative purposes only, and are not meant to unduly limit the scope of the invention in any way.

EXAMPLES

| Phase | Chemical Name | Example 1 | Example 2 |
|---|---|---|---|
| A1 | Dimethicone (and) Dimethicone crosspolymer[1] | 10 | |
| A2 | Cyclopentasiloxane (and) Dimethicone crosspolymer[2] | | 10 |
| A3 | Isododecane | 78 | 78 |
| B1 | Dibutyl Lauroyl Glutamide[3] | 4 | 4 |
| B2 | Dibutyl Ethylhexanoyl Glutamide[4] | 2 | 2 |
| B3 | Isostearyl Alcohol | 6 | 6 |

[1] DC 9041 Silicone Elastomer Blend (15.5% active); Dow Corning
[2] DC 9045 Silicone Elastomer Blend (12.3% active); Dow Corning
[3] Gelatinization Agent GP-1; Ajinomoto
[4] Gelatinization Agent EB-21; Ajinomoto Procedures Phase A ingredients were heated to 120° C. and mixed until uniform. Phase B ingredients were heated to 120° C. and mixed until clear. When both phases are at temperature and both phases appeared clear, phase B was added to phase A and mixed until uniform. The contents were poured into containers and cooled in a −10° C. refrigerator for 20 minutes. They were removed for further characterization and analysis.

| Chemical Name | Example 3 | Example 4 |
|---|---|---|
| Dibutyl Lauroyl Glutamide[3] | 4 | 4 |
| Dibutyl Ethylhexanoyl Glutamide[4] | 2 | 2 |
| Isostearyl Alcohol | 6 | 6 |
| LAURYL POLYDIMETHYLSILOXYETHYL DIMETHICONE/BIS-VINYLDIMETHICONE CROSSPOLYMER, Cyclopentasiloxane[5] | 10 | |
| Lauryl Polydimethylsiloxyethyl Dimethicone/Bis-Vinyldimethicone crosspolymer, Dimethicone[6] | | 10 |
| Isododecane | 78 | 78 |

[3] Gelatinization Agent GP-1; Ajinomoto
[4] Gelatinization Agent EB-21; Ajinomoto
[5] KSG-045Z (25% active); ShinEtsu
[6] KSG-048Z (25% active); ShinEtsu Procedures Phase A ingredients were heated to 120° C. and mixed until uniform. The rest of the ingredients were added to phase A and mixed until uniform. The contents were poured into containers and cooled in −10° C. refrigerator for 20 minutes. They were removed for further characterization and analysis.

What is claimed is:

1. A non-aqueous, structured, gel-form composition containing:
   (a) a low molecular mass N-acyl glutamic acid diamide having a straight-chain alkyl group, comprising dibutyl lauroyl glutamide, which is present in an amount of from about 0.1 to about 10% by weight, based on the weight of the composition;
   (b) a low molecular mass N-acyl glutamic acid diamide having a branched-chain alkyl group, comprising dibutyl ethylhexanoyl glutamide, which is present in an amount of from about 0.1 to about 10% by weight, based on the weight of the composition;
   (c) at least one gel-promoting solvent, which is present in an amount of from about 1.0 to about 20% by weight, based on the weight of the composition;
   (d) at least one silicone elastomer which does not include a polyglycerolated silicone elastomer;
   (e) at least one solvent capable of solubilizing the silicone elastomer; and
   (f) at least one active ingredient, wherein the composition has a hardness value ranging from about 30 to about 300gf, and has a melting point of about 50° C. or higher.

2. The composition of claim 1, wherein (c) is isostearyl alcohol.

3. The composition of claim 1, wherein (d) is employed in an amount of from about 1 to about 40% by weight, based on the weight of the composition.

4. The composition of claim 1, wherein (e) is employed in an amount of from about 5 to about 90% by weight, based on the weight of the composition.

5. The composition of claim 1, wherein (e) is isododecane and the composition is transparent in appearance.

6. The composition of claim 1, which is wax-free.

7. A process for making a non-aqueous, structured, gel-form composition comprising:
   (a) mixing a1) a low molecular mass N-acyl glutamic acid diamide having a straight-chain alkyl group, comprising dibutyl lauroyl glutamide, which is present in an amount of from about 0.1 to about 10% by weight, based on the weight of the composition; a2) a low molecular mass N-acyl glutamic acid diamide having a branched-chain alkyl group, comprising dibutyl ethylhexanoyl glutamide, which is present in an amount of from about 0.1 to about 10% by weight, based on the weight of the composition; a3) at least one gel-promoting solvent, which is present in an amount of from about 1.0 to about 20% by weight, based on the weight of the composition; a4) at least one silicone elastomer which does not include a polyglycerolated silicone elastomer; a5) at least one solvent capable of solubilizing the silicone elastomer; and a6) at least one active ingredient, preferably at a temperature of from about 90° C. to about 125° C., to form a heated composition; and (b) cooling the heated composition to form the non-aqueous, structured, gel-form composition, wherein the composition has a hardness value ranging from about 30 to about 300gf and a melting point of about 50° C. or higher.

8. The process of claim 7, wherein (a3) is isostearyl alcohol.

9. The process of claim 7, wherein (a4) is provided in an amount of from about 1 to about 40% by weight, based on the weight of the composition.

10. The process of claim 7, wherein (a5) is isododecane.

11. The composition of claim 1, wherein the at least one silicone elastomer comprises a polyoxyalkylenated silicone elastomer.

12. The composition of claim 1, wherein the at least one silicone elastomer comprises a non-emulsifying silicone elastomer.

13. A method of making up keratinous tissue, comprising applying the composition of claim 1 to a keratinous tissue.

14. The composition of claim 1, wherein the active ingredient is a colorant.

15. The composition of claim 1, wherein the active ingredient is a sunscreen agent.

* * * * *